United States Patent [19]

Dvorak et al.

[11] 4,456,550

[45] Jun. 26, 1984

[54] VASCULAR PERMEABILITY FACTOR

[75] Inventors: Harold F. Dvorak, Newton Center; Donald R. Senger, Medfield, both of Mass.

[73] Assignee: President and Fellows of Harvard College, Cambridge, Mass.

[21] Appl. No.: 443,209

[22] Filed: Nov. 22, 1982

[51] Int. Cl.$^3$ .................. C07G 7/00; A61K 27/00
[52] U.S. Cl. .................. 260/112 R; 424/85; 424/95; 424/177
[58] Field of Search .................. 260/112 R, 112 B; 424/85, 95, 177; 435/68, 272

[56] References Cited

U.S. PATENT DOCUMENTS

| | | | |
|---|---|---|---|
| 4,335,107 | 6/1982 | Snoeyenbas et al. | 424/88 |
| 4,342,748 | 8/1982 | Pappenheimer et al. | 424/95 |
| 4,348,376 | 9/1982 | Goldenberg | 424/1 |
| 4,359,457 | 11/1982 | Neville et al. | 424/85 |

OTHER PUBLICATIONS

Ooyama et al., Identification and Chromatography of a Vascular Permeability Factor of Renal Origin, Lab Invest., vol. 40(5), 1979, 615–621.
Bacillus–Cerus Toxin, Isolation of Permeability Factor, Ezepchuk et al., Med. Mikrobial Parasitol: 244 (2–3), 1979, 277–284, (USSR) Eng. Abst.
A Vascular Permeability Factor in Lymphocyte Culture Supernatants From Patients . . . Properties, Biomed Express (Paris):23(2), 1975, 73–75, Eng. Abst.
Identification of Both the Pyrogenic and Vascular Permeability Factors . . . In Vitro, Folia Pharmacol. TPN:73(i), 1977, 63–71, Eng. Abst.
Dvorak et al., J. Immunol., vol. 122, 166–174, (1979).

*Primary Examiner*—John Kight, III
*Assistant Examiner*—Garnette D. Draper

[57] ABSTRACT

A purified vascular permeability protein factor and method of manufacture, wherein the factor has the following characteristics:

(a) in an aqueous solution (0.01 M $Na_3PO_4$, pH 7) whose concentration of NaCl is varied linearly, the factor is eluted from a heparin-Sepharose chromatography column in a peak centered at 0.4 M NaCl;

(b) in an aqueous solution of $Na_3PO_4$ (pH 7.0) whose concentration is varied linearly, the factor is eluted from a hydroxylapatite column in a peak centered at 0.25 M $Na_3PO_4$;

(c) when subjected to SDS gel electrophoresis in a 7.5% polyacrylamide slab gel (0.375 M tris-HCl (pH 8.8), 0.1% SDS) at 35 milliamps and 4° C., the factor is localized to a region corresponding to a molecular weight between 34,000 and 45,000 daltons.

9 Claims, No Drawings

VASCULAR PERMEABILITY FACTOR

BACKGROUND OF THE INVENTION

The invention described herein was made with Government support and the U.S. Government has certain rights in the invention.

This invention relates to a novel factor which increases the permeability of blood vessels and to antibodies directed against such a factor. The factor may be isolated from serum-free culture medium of carcinoma and sarcoma tumor cells or from tumor ascites fluids.

It is known that cultures of tumor cells produce factors that activate host inflammatory pathways. Specifically, Dvorak et al., Journal of Immunology, 122:166 (January, 1979) discloses four such factors, including a vascular permeability factor. Until now, however, there has been no indication of the existence of a distinct substance as outlined below that can be isolated, purified and characterized; nor has there been any indication that antibodies may be raised against such a substance.

SUMMARY OF THE INVENTION

The substance according to the invention is a purified protein which affects vascular permeability and has the following characteristics:

(a) In an aqueous solution (0.01 M $Na_3PO_4$, pH 7.0) whose concentration of NaCl is varied linearly, the factor is eluted from a heparin-Sepharose chromatography column in a peak centered at a concentration of 0.4 M NaCl.

(b) In an aqueous solution of $Na_3PO_4$ (pH 7.0) whose concentration is varied linearly, the factor is eluted from a hydroxylapatite column in a peak centered at a concentration of 0.25 M $Na_3PO_4$.

(c) When subjected to SDS gel electrophoresis in a 7.5% polyacrylamide slab gel (0.375 M Tris-HCl (pH 8.8), 0.1% SDS) at 35 milliamps and 4° C., the factor is localized to a region corresponding to a molecular weight between 34,000 and 45,000 daltons.

The factor displays a remarkable ability to increase vascular permeability, one mole being equivalent in that respect to 800 moles of histamine. Moreover, the factor is not significantly toxic to blood vessels or endothelial cells and does not cause mast cell degranulation.

In its preferred form, the protein factor is unaffected by the presence of soybean trypsin inhibitor, mepyramine, cimetidine, pepstatin A, promethazine or indomethacin; the factor may be derived from fluids that are biologically generated by mammalian tumor cells including: guinea pig hepatocarcinomas, line 10 or line 1, guinea pig 104 Cl fibrosarcoma, hamster HSV-NIL8 sarcomas, rat sarcomas B77 Rat 1 and RR 1022, mouse TA3-St carcinoma, MOPC 21 myeloma, and polyoma Balb/c 3T3 sarcoma.

The factor has therapeutic value insofar as it enables blood nutrients to reach tissue with increased need for nutrients, as in wound healing. The antibody generated in response to the factor has therapeutic value insofar as it blocks a tumor's ability to increase vessel permeability and thereby to obtain nutrients from increased vessel "leakage".

DESCRIPTION OF THE PREFERRED EMBODIMENTS

According to one presently preferred embodiment, the factor is a protein secreted by line 10 "hepatocarcinoma" (bile duct carcinoma) (hereinafter, "line 10 cells"), an ascites varient of a tumor induced in Sewall-Wright-inbred strain 2 guinea pigs with the water-soluable carcinogen diethylnitrosamine.

PURIFICATION OF THE PROTEIN

The protein may be purified from ascites fluid of guinea pigs injected intraperitoneally with line 10 cells, or from serum-free culture medium of the line 10 cells, as evidenced by the following examples.

EXAMPLE 1

(Purification From Serum-Free Culture)

Line 10 tumor cells are induced, ascites variants are formed, and transplantation is performed according to techniques previously reported, e.g., Rapp et al., J. Nat'l. Cancer Inst. 41:1 (1968); and Churchill et al., J. Nat'l. Cancer Inst. 41:13 (1968).

After the tumor cells are passaged (10 to 30 million cells) at intervals of 7 to 10 days in the peritoneal cavities of the guinea pigs, 20 ml of Hanks' balanced saline solution (HBSS) and 200 units of heparin (Liquaemin, Organon Inc., W. Orange, N.J.) are injected into the peritoneal cavity and the tumor cells are recovered. The cells then are washed three times in cold Hanks' balanced saline solution (HBSS), counted, and suspended at a concentration of about $2.5 \times 10^6$ cells per ml in Dulbecco's modified Eagle's medium having a glucose concentration of 4 g/l and including 50 units/ml penicillin and 50 μg/ml streptomycin. Various other media known to support line 10 cells could also be used. The solution is transferred to Falcon flasks to be cultured at 37° C. in a humidified, $CO_2$ enriched (5%) atmosphere for approximately 18 hours.

To harvest the protein, the culture is centrifuged at 10,000 G for 20 minutes and the cell-free supernatant is recovered.

The protein is isolated and purified approximately 1800 fold from the serum-free conditioned medium by the following procedure. Approximately two (2) liters of line 10 culture medium containing about 20 μg of protein per ml is passed over and bound to a 40 ml heparin-Sepharose column. A linear gradient of NaCl in an aqueous solution (buffered with 0.01 M $Na_3PO_4$, pH 7.0) is passed through the column. The protein is eluted as a peak centered at a concentration 0.40 M NaCl. The active fraction thus eluted from the heparin-Sepharose column is dialyzed against phosphate buffered saline solution (PBS). It is then passed over and bound to a 5 ml hydroxylapatite column. The protein is then eluted in a linear gradient of aqueous $Na_3PO_4$ (pH 7). The active fraction is eluted as a peak centered at 0.25 M $Na_3PO_4$.

The fraction thus eluted is subjected to gel electrophoresis using sodium dodecyl sulfate (SDS) 7.5% polyacrylamide slab gels such as described in U. K. Laemmli, Nature 227:680–685 (1970).

Electrophoresis is performed on non-reduced, unheated samples at 4° C. SDS concentration in all buffers is 0.1%. Electrophoresis is performed at a constant current of 35 milliamps until the bromophenol blue marker reaches the end of the slab (about 1¾–2 hours).

To recover the protein after electrophoresis the gels are sliced and each slice is pulverized in two volumes of PBS with a tissue grinder. The resulting suspensions are dialyzed for 20 hours at 4° C. against repeatedly changed PBS.

To determine molecular weight, samples are compared to the following molecular-weight markers (each of which is reduced before electrophoresis):

|  |  | MW |
|---|---|---|
| Phosphorylase b | (rabbit muscle) | 94,000 |
| Albumin | (bovine serum) | 67,000 |
| Ovalbumin | (egg white) | 43,000 |
| Carbonic Anhydrase | (bovine erythrocyte) | 30,000 |
| Trypsin Inhibitor | (soybean) | 20,100 |

Electrophoresis localizes the protein into a region which represents, according to the above markers, a molecular weight centered between 38 and 40 K daltons and substantially entirely contained between a point representing 34 K daltons and a point representing 45 K daltons.

EXAMPLE 2

The procedure described in example 1, above is followed, but the protein is purified (about 10,000 fold) from ascites fluid rather than from the serum free culture.

The Vascular Permeability Increasing Activity Of The Protein

The protein's ability to increase vascular permeability may be quantified by measuring its effect on influx of radioactive iodine-labeled human serum albumin ($^{125}$I-HSA). Specifically, there is a marked influx of $^{125}$I-HSA as early as one hour after intraperitoneal injection of line 10 tumor cells.

EXAMPLE 3

Guinea pigs are injected intraperitoneally with saline, macrophages, line 10 tumor cells, or purified permeability factor. Immediately thereafter the animals received $5 \times 10^6$ cpm $^{125}$I-HSA intravenously. One hour later the animals are exsanguinated under ether anesthesia and peritoneal fluid is collected following i.p. injection of 20 ml of heparinized (10 units/ml) Hanks' balanced salt solution (HBSS). Animals injected with line 10 tumor cells or the purified permeability factor exhibited marked increase in $^{125}$I-HSA influx into ascites fluid as compared with controls where influx is measured by $$\text{Influx} = \frac{\text{total } dpm\ ^{125}I\text{-}HSA \text{ in ascites}}{dpm\ ^{125}I\text{-}HSA \text{ per ml of blood}}$$

As little as 200 ng ($5 \times 10^{-12}$ moles) of purified material increases vascular permeability equivalent to 1.25 µg ($4 \times 10^{-9}$ moles) of histamine.

EXAMPLE 4

The Miles assay (described below) is another means of establishing the protein's effect on vascular permeability.

Depilated (Nair) Hartley guinea pigs are injected (i.v.) with 1 ml of 0.5% Evans Blue dye in phosphate buffered saline. Line 10 cells are cultured ($1 \times 10^6$ cells/ml) in serum-free Dulbecco's modified Eagle's medium described in example 1 above and the medium is harvested at 1, 5 and 24 hours respectively. Samples (0.2 cc) of the medium in isotonic solution and at neutral pH are injected intradermally. Line 10 culture media as well as the purified permeability factor cause blueing at the site of intradermal injection within 5 minutes, whereas control media causes no blueing.

Physiological Effects of the Protein

The factor's physiological effects are further demonstrated by colloidal carbon labeling in guinea pigs. Specifically, guinea pigs were implanted intraperitoneally with $3 \times 10^7$ line 10 cells, and, 7 days later, were injected intravenously with colloidal carbon. Examination of the peritoneal linings of such animals reveals that many venules of the peritoneal wall, diaphragm, mesentery, and gastrointestinal serosal surfaces are heavily labeled with colloidal carbon. Comparable vessels in animals not subjected to line 10 or other tumors are not labeled.

As determined by light microscopy (1 µm Epon sections) and electron microscopy, the factor does not cause endothelial cell damage or mast cell degranulation. Vessels respond equally well to multiple challenges with equivalent doses of protein administered 30 min. apart; the effect of a single intradermal injection is rapid (within 5 min.) and transient (little residual increased permeability detectable 20 min. after injection), providing further evidence that protein is not toxic to blood vessels.

The factor is distinct from known vascular permeability factors as evidenced by the fact that:

(1) unlike PF/dil, the factor is not inhibited by soybean trypsin inhibitor (e.g. 200 µg/ml up to 1000 µg/ml);
(2) unlike leukokinins, the factor is not sensitive to pepstatin A (20 µM);
(3) unlike lymphocyte PF's of similar molecular weight, the factor does not exhibit a latency period before increasing vascular permeability;
(4) unlike substances which are mediated by histamine release, the factor's activity is not affected by antihistamines (e.g. promethazine) or by the presence of histamine $H_1$- and $H_2$- receptor antagonists (e.g., mepyramine 5 µmole/kg s.c.; t, $-30$ min. and cimetidine 500 mole/kg s.c.; t, $-30$ min.); and
(5) unlike prostaglandins the factor is not affected by either systemic (5 mg/kg i.p. 25 hr. and 1 hr. prior to skin test) or local intradermal (10 µM) treatment with indomethacin at the site of skin test.

Factor synthesis in serum-free culture medium is blocked by cycloheximide (20 µg/ml, 90 min. period inclubation, 3 hour culture).

The Antibody To The Protein

To make the antibody, purified VPM protein (about 10 µg), prepared as described above in Example 1, in a polyacrylamide gel slice is homogenized (Dounce) in an equal volume of complete Freund's adjuvant (total volume about 5 ml). Animals are given intradermal injections on each side and on each leg below the knee and at four SC cites: Immunization is repeated 6 weeks after the initial immunization as described above, but incomplete (without the mycobacterial component) Freund's adjuvant is used. Eleven weeks after initial immunization, 10 µg of purified VPM protein is extracted from polyacrylamide gel by homogenization in 2 ml phosphate buffered saline solution. The resulting extract is injected at two sites (1 ml at each site).

The antibody is present in immunoglobulin (Ig) purified from blood of rabbits so injected. Specifically, the serum Ig is bound to a protein A sepharose column and antibody eluted with a high-salt-concentration or low-pH aqueous solution.

The ability of the antibody to block vascular permeability is demonstrated by tests similar to those which establish the factor's permeability mediating effect.

EXAMPLE 6

Control guinea pigs are treated with $^{125}$I-HSA and line 10 tumor cells as in Example 3, above. A test group of guinea pigs is subjected to the same conditions, except that the i.p. injection of tumor cells includes antibody prepared as described above. Specifically, 0.2 ml of antibody (2 mg of IgG) is injected with $3 \times 10^7$ line 10 tumor cells in 5 ml of HBSS. The test group exhibits a 79% reduction in the influx of $^{125}$I-HSA as compared to the control.

EXAMPLE 7

Control guinea pigs are tested in the Miles assay as in Example 4, and test guinea pigs are treated in the same way with the addition of antibody prepared as described above. For test animals, 80 μl (0.8 mg) of immune IgG blocks the permeability factor in 1 ml of line 10 ascites fluid obtained 7 days after injection of $3 \times 10^7$ tumor cells.

Other Tumors

The above examples relate to line 10 tumor cells in guinea pigs. Other guinea tumor cells, and tumor cells from other mammals such as rats and mice also secrete permeability increasing activity in serum-free culture. For example TA3-St mouse carcinoma cells, MOPC 21 myeloma cells and polyoma Balb/c 3TC sarcoma cells, HSV-NIL8 hamster sarcoma cells, B77 Rat 1 and RR 1022 rat sarcoma cells, and guinea pig 104Cl fibrosarcoma cells all secrete vascular permeability increasing activity.

EXAMPLE 8

A/Jax mice injected with TA3-St carcinoma tumor cells were subjected to the procedures described above in Example 3, (using $1 \times 10^6$ cpm $^{125}$I-HSA and 5 ml of heparinized HBSS). The animals showed marked increase in $^{125}$I-HSA influx compared to controls (saline and macrophages).

EXAMPLES 8 AND 9

Hartley guinea pigs were subjected to the procedures described in Example 4 using serum-free media from either mouse TA3-St tumor or hamster HSV-NIL 8 tumor respectively. In all cases the skin showed blueing at the site of intradermal injection within 5 minutes, whereas saline controls exhibited no response.

EXAMPLE 10

Antibody raised in response to line 10 tumor cells is used as in Example 7 with similar results in blocking the line 1 tumor cell factor. Antibody raised in response to permeability factor generated in a culture of line 10 tumor cells is also effective in blocking guinea pig 104Cl fibrosarcoma tumor cell factor.

What is claimed is:

1. A fast-acting purified protein factor which affects vascular permeability within 5 minutes of the time of injection and has little residual effect 20 minutes after injection and has the following characteristics:
   (a) in an aqueous solution (0.01 M Na$_3$PO$_4$, pH 7) whose concentration of NaCl is varied linearly, the factor is eluted from a heparin-Sepharose chromatography column in a peak centered at 0.4 M NaCl;
   (b) in an aqueous solution of Na$_3$PO$_4$ (pH 7.0) whose concentration is varied linearly, the factor is eluted from a hydroxylapatite column in a peak centered at 0.25 M Na$_3$PO$_4$;
   (c) when subjected to SDS gel electrophoresis in a 7.5% polyacrylamide slab gel (0.375 M tris-HCl (pH 8.8), 0.1% SDS) at 35 milliamps, 4° C., the factor is localized to a region corresponding to a molecular weight between 34,000 and 45,000 daltons.

2. The factor of claim 1 further characterized in that one mole of said factor increases vascular permeability by an amount equivalent to 800 moles of histamine.

3. The factor of claim 1 wherein the vascular permeability activity of said factor is unaffected by the presence of an inhibitor selected from the group consisting of soybean trypsin inhibitor, pepstatin A, promethazine, mepyramine, cimetidine, and indomethacin.

4. The factor of claim 1 wherein said factor is derived from fluids that are biologically generated by mammalian tumor cells selected from the group consisting of sarcoma and carcinoma cells.

5. The factor of claim 4 wherein said tumor cells are selected from the group consisting of line 10 and line 1 bile duct carcinoma guinea pig cells, TA3-St mouse carcinoma cells, HSV-NIL8 hamster sarcoma cells, B77 Rat 1 and RR 1022 rat sarcoma cells, 104 Cl fibrosarcoma guinea pig cells, MOPC 21 myeloma cells, and Balb/c 3T3 sarcoma cells.

6. A therapeutic agent comprising a protein factor according to claim 1 and a non-toxic therapeutically acceptable carrier.

7. A purified antibody generated in response to a factor according to claim 1.

8. A therapeutic agent comprising an antibody according to claim 7 and a non-toxic therapeutically acceptable carrier.

9. A method of making a fast-acting purified protein factor for controlling vascular permeability comprising the following steps:
   (a) incubating tumor cells in an environmental medium, said tumor cells being selected from the group comprising sarcoma and carcinoma tumor cells;
   (b) separating said cells from said medium;
   (c) purifying said factor from said medium;
   wherein said purification step comprises subjecting a fluid containing said protein to SDS gel electrophoresis and collecting said protein from a region corresponding to a molecular weight between 34,000 and 45,000.

* * * * *

UNITED STATES PATENT AND TRADEMARK OFFICE
CERTIFICATE OF CORRECTION

PATENT NO. : 4,456,550
DATED : June 26, 1984
INVENTOR(S) : Harold F. Dvorak et al.

It is certified that error appears in the above-identified patent and that said Letters Patent is hereby corrected as shown below:

On the title page, Assignee should read -- The Beth Israel Hospital Association, Boston, Mass. --.

Column 1, lines 6 to 8, cancel "The invention described herein was made with Government support and the U.S. Government has certain rights in the invention.".

Signed and Sealed this

Fourteenth Day of May 1985

[SEAL]

Attest:

DONALD J. QUIGG

Attesting Officer     Acting Commissioner of Patents and Trademarks